United States Patent [19]

Arru et al.

[11] Patent Number: 4,758,151

[45] Date of Patent: Jul. 19, 1988

[54] APPARATUS FOR MANUFACTURE OF VALVE FLAPS FOR CARDIAC VALVE PROSTHESES

[75] Inventors: Pietro Arru; Gioacchino Bona, both of Turin; Maria Curcio, Saluggia; Franco Vallana, Turin, all of Italy

[73] Assignee: Sorin Biomedics S.p.A., Saluggia, Italy

[21] Appl. No.: 871,861

[22] Filed: Jun. 6, 1986

Related U.S. Application Data

[62] Division of Ser. No. 634,085, Jul. 25, 1984, Pat. No. 4,624,822.

[30] Foreign Application Priority Data

Jul. 25, 1983 [IT] Italy .................. 67802 A/83

[51] Int. Cl.$^4$ .............................................. B29C 51/10
[52] U.S. Cl. ........................................ 425/388; 425/392; 425/446
[58] Field of Search ............... 425/85, 387.1, 388, 425/392, 446; 623/2

[56] References Cited

U.S. PATENT DOCUMENTS

| | | | |
|---|---|---|---|
| 582,440 | 5/1897 | Stifel | 210/416.3 |
| 2,342,035 | 2/1944 | Clark | 210/416.1 |
| 2,448,157 | 8/1948 | Schneider | 210/416.1 |
| 4,024,064 | 5/1977 | Rakowicz et al. | 210/416.1 |
| 4,084,268 | 4/1978 | Ionescu | 3/1.5 |
| 4,443,895 | 4/1984 | Lane | 623/2 |
| 4,470,157 | 9/1984 | Love | 623/2 |
| 4,473,423 | 9/1984 | Kolff | 623/2 |
| 4,477,930 | 10/1984 | Totten et al. | 623/2 |

FOREIGN PATENT DOCUMENTS

| | | | |
|---|---|---|---|
| 156583 | 10/1921 | United Kingdom | 210/183 |
| 2046165 | 11/1980 | United Kingdom | |

*Primary Examiner*—Willard E. Hoag
*Attorney, Agent, or Firm*—Hedman, Gibson, Costigan & Hoare

[57] ABSTRACT

A vacuum forming apparatus for fixing and shaping animal tissue into the shape of a cardiac valve prosthesis, including a tapered form, with elongated through apertures, suspended in a reservoir of fixative and vacuum means for producing a reduced pressure within the tapered form.

8 Claims, 4 Drawing Sheets

APPARATUS FOR MANUFACTURE OF VALVE FLAPS FOR CARDIAC VALVE PROSTHESES

This is a divisional of application Ser. No. 634,085, filed July 25, 1984, now U.S. Pat. No. 4,624,822.

The present invention relates to methods for the manufacture of valve flaps of biological tissue for cardiac valve prostheses.

Cardiac valve prostheses provided with biological tissue valve flaps are currently utilised in clinical practice.

A prosthesis of this type is described, for example, in U.S. Pat. No. 4,084,268.

Cardiac valve prostheses including valve flaps of biological tissue exhibit a more restricted thrombogenic activity and reproduce the fluodynamic process which characterises the operation of natural cardiac valves with greater fidelity than cardiac prostheses comprising a rigid frame within which are mounted one or more shutters oscillating under the thrust of the flow of blood.

To form such prostheses it has been proposed to fit a natural cardiac valve, for example a pig's aortic valve, onto a support frame. This solution is, however, inconvenient to put into practice, given the difficulty of easily obtaining a good natural starting material.

Another solution, which is very much more advantageous and functional, is to make the valve flaps of the prosthesis starting from biological tissue such as animal pericardium, preferably taken from cattle or pigs. The use of membranes of fascia lata or of dura mater of heterologous, homologous or autologous origin has also been proposed.

After removal, the tissue intended to be used for making the valve flaps is subjected to a cleaning operation and to a direct selection to retain only those parts of it which are structurally most suitable.

The biological tissue is subsequently subjected to a treatment, called "fixation", performed, for example, by immersion in glutaraldehyde at a controlled pH, possibly enriched with anticalcifying additives. The fixation treatment (or "stabilisation" is another currently used term) is intended to encourage the establishment of cross links between the various forms of glutaraldehyde and the amino groups of proteins constituting the collagen of the tissue.

After the final fixation of the biological tissue, a cycle of cutting and shaping operations permits the required shape to be imparted to the valve flaps for mounting in the frame of the prosthesis.

After mounting in the frame of the prosthesis, during conservation before implanting in the patient, biological tissue valve flaps are normally "held in shape", for example by means of cotton wads introduced between the frame and the valve flaps. Biological tissue which is completely fixed before shaping, in fact tends to revert to its natural flat conformation.

Patent specification No. GB-A 2 046 165 addresses the problem of obtaining a good fit between the biological tissue which forms the valve flaps and the frame of a cardiac prosthesis both in the case in which a natural valve, such as a pig's aortic valve, is mounted in the frame and in the case in which the valve flaps are made starting from sheets of biological tissue such as pericardium. For this purpose it is proposed that the final fixation of the biological tissue take place after mounting it in the frame.

In the case in which the valve flaps are made starting from sheets of biological tissue, the incompletely fixed tissue is cut and applied to the frame in such a way as to form three approximately shaped flaps. The supporting frame with the biological tissue flaps applied thereto is then clamped between two complementary dies intended to impart the final shape to the valve flaps. The assembly thus obtained is then immersed in a liquid based on glutaraldehyde which effects the final fixation of the tissue of the valve flaps whilst these are subjected to the action of the shaping dies.

This solution makes it possible to overcome the typical disadvantage of prostheses the valve flaps of which are made from sheets of biological tissue completely fixed before the shaping of the flaps and their mounting in the frame. As previously indicated, in such prostheses, the valve flaps naturally tend to re-sume their natural flat conformation.

However, the process described in specification No. GB-A-2046165 does not permit the resolution of a particularly sensitive problem, that is to say that of stress which is imparted to the biological tissue sheets upon mounting in the frame of the prosthesis and upon shaping of the valve flaps. The biological tissue is in fact mounted in the frame, typically by sewing, before the shaping of the flaps is effected. The performance of the shaping operation involves, among other things, the application of deformation forces to the parts of the biological tissue connected to the frame. The tissue can therefore be weakened in these parts with the consequent risk of rupture of the prosthesis or, at least, a significant reduction in the useful life of the prosthesis.

The shaping of the valve flaps by mechanical stamping means further involves, intrinsically, the application of stresses to the valve flaps.

The same specification No. GB-A-2 046 165 also describes a process for obtaining a cardiac prosthesis constituted by a frame in which there is mounted a pig's aortic valve. In this case the biological tissue is fixed by immersing the prosthesis in a container filled with fixation liquid. In particular, the prosthesis is applied to close the lower end of a vertical tubular duct in which a column of fixation liquid is maintained, sufficient to ensure that between the two sides of the prosthesis a certain pressure difference is established. This pressure difference encourages the establishment of a precise fit between the frame and the natural valve.

In this case, however, no shaping action of the valve flaps occurs since the flaps of the valves already have the necessary arcuate or bowl shape conformation. Moreover the technique of fixation under a liquid pressure gradient described in specification No. GB-A 2 036 165 is not directly applicable to prostheses in which the valve flaps are made from sheets of biological tissue such as pericardium. In this case, in fact, the parts of the tissue defining the valve flaps of the prosthesis do not have, before shaping, the necessary matching shape to ensure a liquid-tight seal between the sides of the prosthesis.

The object of the present invention is to provide a process for making valve flaps of biological tissue for cardiac valve prostheses capable of being put into practice economically on an industrial scale, overcoming the disadvantages of the prior art processes described above.

This object is achieved, according to the present invention, by a process for making, from sheets of biological tissue, valve flaps for cardiac valve prostheses in which the said flaps are mounted in a support frame and in which sheets of incompletely fixed biological tissue, including portions which can define the said valve flaps, are subjected to final fixation whilst the said portions are maintained in a conformation substantially identical to the conformation of the valve flaps when mounted in the prosthesis, characterised by the fact that it comprises the operations of:

providing forming means for the said sheets of biological tissue, capable of separating from each other in a substantially fluid-tight manner the opposite faces of said valve flap defining portions applying the said sheets of biological tissue to the said forming means, generating a fluid pressure difference between the opposite separated faces of the said portions to produce the deformation of these portions towards the said conformation substantially identical to the conformation of the valve flaps when mounted in the prosthesis, effecting the final fixation of the biological tissue, and separating the said sheets of biological tissue from the said forming means for subsequent mounting in the support frame.

The process of the invention allows valve flaps of biological tissue for cardiac prostheses to be made economically with characteristics of high reliability and durability.

The deformed shape in which the biological tissue of each flap is finally fixed is, in fact, that in which the flap itself is mounted in the prosthesis. In other words, since the fixation is effected in a deformed shape the valve flap stably assumes this deformed shape and tends spontaneously to return to this latter even after having been stretched from this shape under the action of the flow of blood.

The process of the invention therefore allows a precise shaping of the valve flaps before assembly in the prosthesis.

It is moreover possible to perform the shaping of the valve flaps whilst the flaps themselves are subjected to a pressure range which substantially reproduces the pressure range to which the flaps are subjected in use. In particular, in prostheses provided with several valve flaps it is possible to impart to the flaps themselves, upon final fixation of the biological tissue, a mutually matching configuration which can be exactly reproduced in the conditions of use.

With the process according to the invention, then, the risk of deformation stresses being imparted to the biological tissue is completely eliminated, particularly in the region of connection to the frame. The biological tissue is in fact mounted (sewn) to the frame after having been finally fixed and shaped in the final conformation of use. With shaping under fluid pressure the intrinsic disadvantages of mechanical shaping by stamping are also avoided.

The invention relates in particular to a process for making valve flaps for cardiac prostheses comprising a frame capable of being traversed by a flow of blood and a sleeve of biological tissue with a plurality of valve flaps anchored to the frame along respective crescent shape edges and provided with free edges, projecting inwardly of the frame, and able to be separated by blood flowing through the prosthesis in one direction and to prevent the flow of blood in the opposite direction by moving to closely matching positions under the pressure exerted by the blood itself, characterised by the fact that it comprises, in order, the operations of:

providing a sleeve-forming element of substantially tubular form the wall of which has angularly adjacent apertures corresponding in number to the number of valve flaps of the sleeve and separated from one another by shaped wall elements extending in an axial direction with respect to the forming element; the said apertures having corresponding end edges the shape of which reproduces the shape of the said crescent shape edges of the valve flaps of the sleeve, sealingly fitting a tubular sheath of incompletely fixed biological tissue onto the said forming element, establishing between the interior of the forming element and the exterior of the said element a pressure difference such that the portions of the sheath of biological tissue facing the said apertures of the forming element are pressed inwardly of the said cavity in an arrangement in which the portions of the sheath deformed by the effect of such pressure difference converge radially inwardly into the forming element in partially matching condition and each has at least one crescent shaped edge, effecting the final fixation of the biological tissue of the sheath whilst maintaining the said pressure difference between the interior cavity of the forming element and the exterior of the element itself such that each of the said portions assumes, in a substantially stable manner, by virtue of such final fixation, the deformed conformation achieved by the effect of the said pressure difference, and separating the finally fixed biological tissue of the sheath along a line joining the ends of the crescent shaped edges of the said portions of the stably deformed sheath to create, in each of such portions, a free edge defining the free edge of one of the valve flaps of the sleeve.

According to another aspect, the present invention provides apparatus for the production of valve flaps for cardiac prostheses comprising a frame which can be traversed by a flow of blood and a sleeve of biological tissue with a plurality of valve flaps anchored to the frame along respective crescent shaped edges and provided with free edges, projecting inwardly of the frame, able to be separated by blood flowing through the prosthesis in one direction and to prevent the flow of blood in the opposite direction by moving to closely matching positions under the pressure exerted by the blood itself, characterised by the fact that it comprises, a reservoir which can be filled with a fluid for the fixation of the biological tissue, at least one forming element for the said sleeve, projecting into the said reservoir in a position immersed in the said fixation liquid, the said forming element being of substantially tubular form with a peripheral wall traversed by adjacent apertures, equal in number to the number of valve flaps of the sleeve, separated from one another by shaped wall elements extending in an axial direction with respect to the forming element; the said apertures having corresponding edges the shape of which reproduces the shape of the crescent shaped edges of the valve flaps of the sleeve, and means for establishing a pressure difference between the fixation fluid within the reservoir and the interior cavity of the said forming element.

The invention will now be described, purely by way of non limitative example, with reference to the attached drawings, in which.

Figure 7:
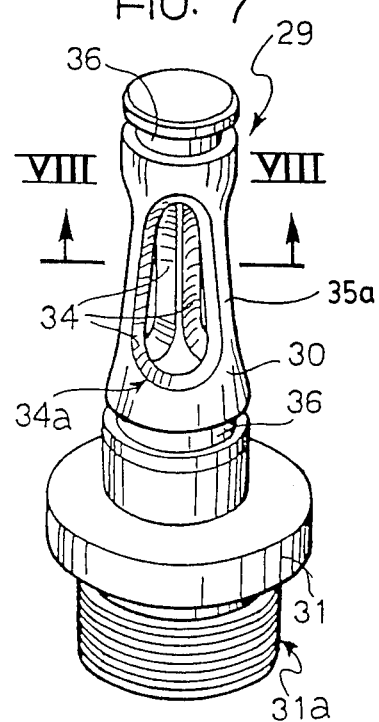
Figure 8:
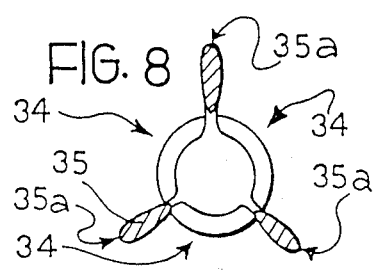
Figure 6:
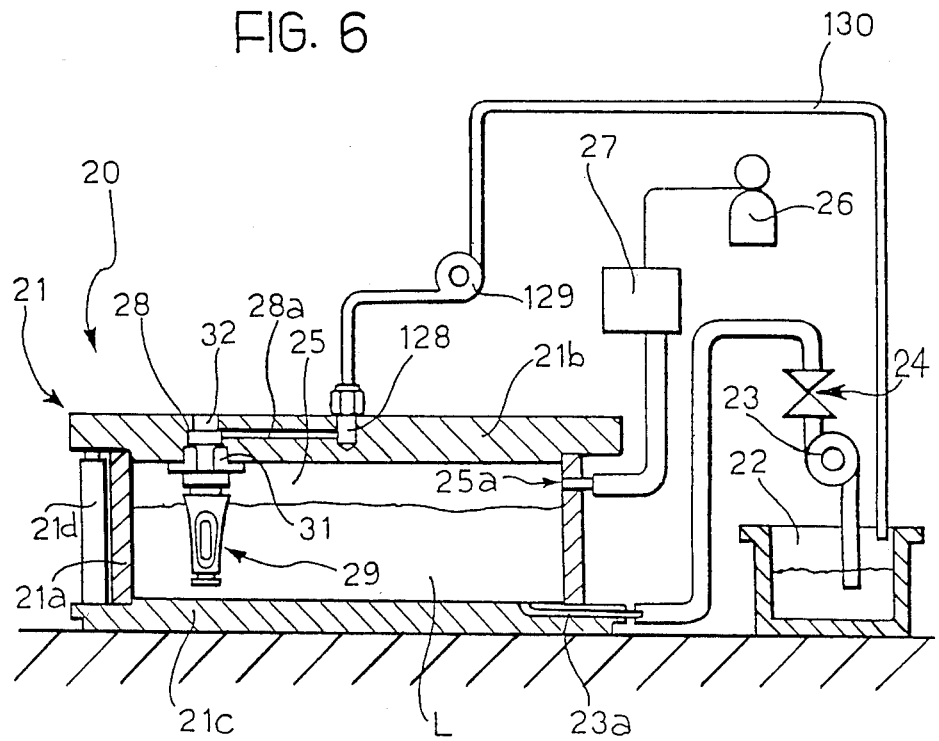

FIG. 6 schematically illustrates apparatus for the performance of the invention;

FIG. 7 is a perspective view on an enlarged scale of one of the elements of the apparatus of FIG. 6;

FIG. 8 is a section taken on the line VIII—VIII of FIG. 7, and

FIGS. 9 to 12 schematically illustrate various successive stages in the process of the invention.

Figure 1:
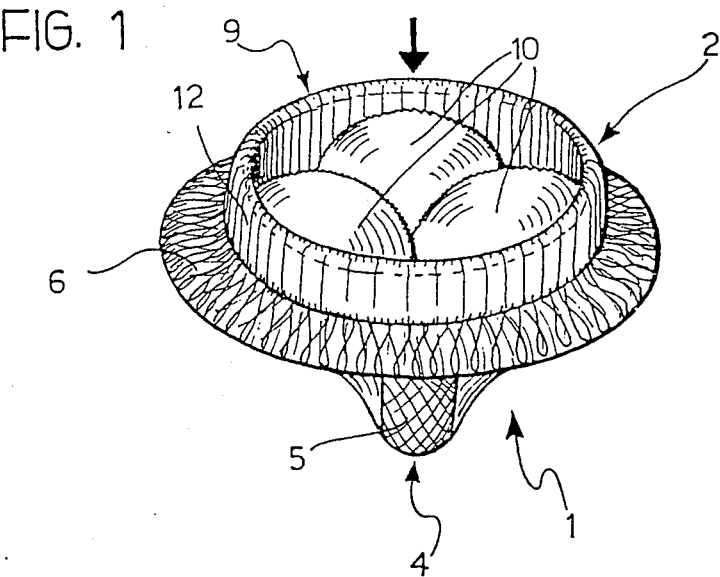
FIG. 1 is a perspective view of a cardiac valve prosthesis provided with valve flaps formed according to the invention.
Figure 2:
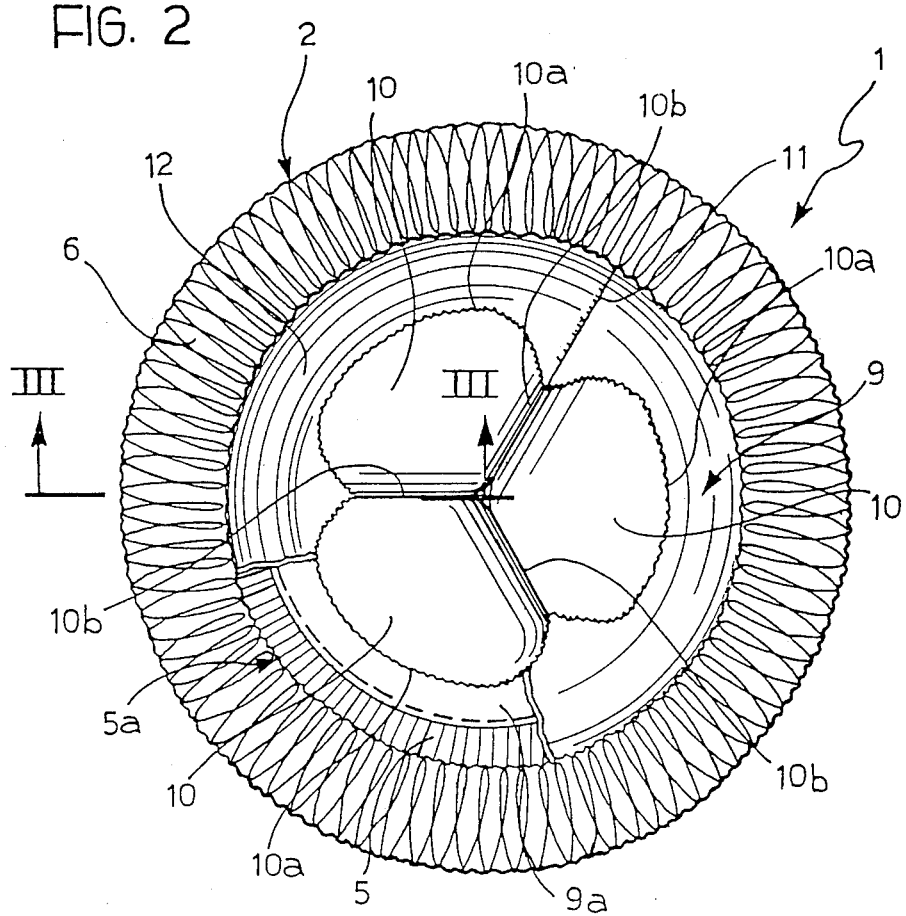
FIG. 2 is an axial view from above of the valve prosthesis of FIG. 1.
Figure 3:
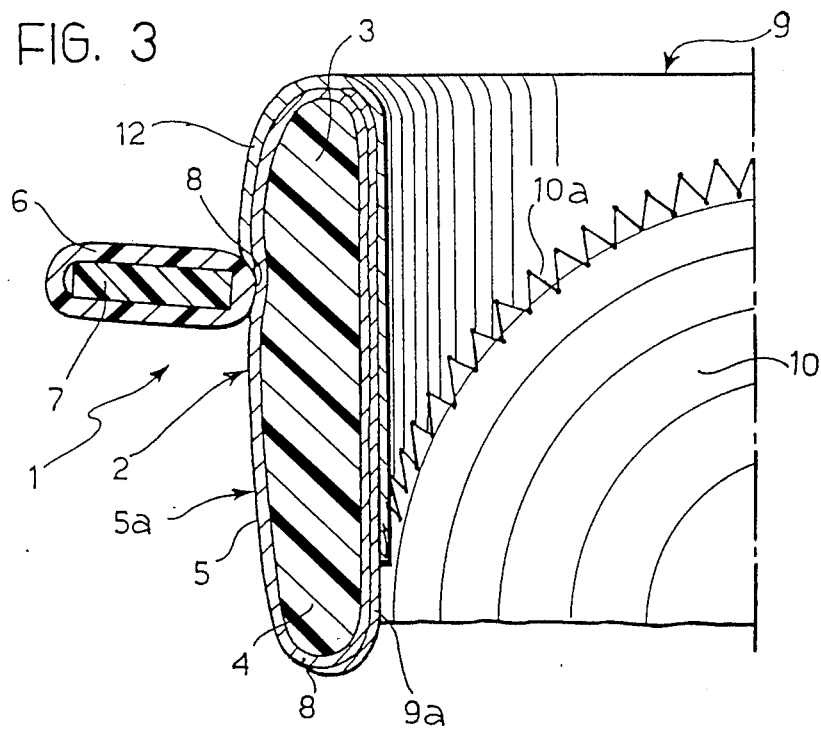
FIG. 3 is a section taken on the line III—III of FIG. 2.

In FIGS. 1 to 3 a cardiac valve prosthesis is generally indicated by the reference numeral 1; this is intended to be implanted in a cardiac wall to replace a natural valve.

In the implantation position the prosthesis is sutured to the cardiac wall in the zone surrounding the orifice formed by removal of the autologous valve membranes.

Structurally, the prosthesis is constituted by a support structure (frame) of generally annular form, which is intended to be sutured to the cardiac wall and to receive within it a valve sleeve including valve flaps of biological tissue. As is known to the expert in the art and as will be better illustrated below, the prosthesis is intended to be traversed by a flow of blood in the direction schematically indicated by the arrow in FIG. 1 and to prevent the flow of blood in the opposite direction.

The frame of the prosthesis, generally indicated 2, includes a rigid or semi-rigid stent having a set of three shaped projections 4 (FIG. 3).

The stent 3 and the projections 4 are normally constituted by a single piece of biocompatible material such as, for example, titanium, a chrome-cobalt alloy or one based on cobalt, or else the plastics materials known by the commercial names "Teflon" or "Delrin".

The stent 3 and the projections 4 are encased in a biocompatible textile 5 such as, for example, a textile made with the yarn known by the commercial name "Dacron".

The textile 5 forms, on the outer face of the stent 3, a wide annular loop 6 constituting a ring for the suture of the prosthesis to the cardiac tissue.

Within the loop 6 there is normally provided an annular pad 7 of biocompatable material, constituting a reinforcing core for the suture ring of the prosthesis. The pad 7 is constituted by a ring of fabric which can easily be traversed by the surgical thread utilised for the suture of the prosthesis to the cardiac tissue.

The textile 5 is wound around the stent 3 and subsequently closed in a generally tubular configuration by suture stitches indicated 8.

In the embodiment of FIGS. 1 to 3, suture stitches 8 are disposed in correspondence with the terminal edge of the stent 3 from which the projections 4 extend and in correspondence with the region of connection of the suture ring 6,7. Other arrangement for achieving the same final result are naturally possible.

To the textile 5, and possibly also on the thread constituting the suture stitches 8, there is applied (before or after mounting on the stent 3) a coating of biocompatable carbonaceous material 5a constituted, for example, by graphite, glassy carbon or carbon having a turbostratic structure.

The coating 5, which significantly improves the antithrombogenic properties of the textile 5, is applied by cathodic spraying (sputtering) utilising a target constituted by a carbonaceous material, normally selected from the group comprising graphite, glassy carbon and carbon with a turbostratic structure.

The application by cathodic spraying is described in a detailed manner in Italian Patent Application No. 67,978-A/82, by the same applicant, the description of which is incorporated herein by reference. The application of the coating 5a by cathodic spraying can be effected at a temperature close to ambient temperature, avoiding damage to the textile 5 or the material of the stent 3 in the case in which the coating 5 is applied after the textile 5 has been fixed to the core 3.

The interior part of the prosthesis 1 is occupied by a valve sleeve 9 of biological tissue including three valve flaps indicated 10.

The sleeve 9 is made of an inert biological material. Biological tissues which have been used with success are cow or pig pericardium tissues, although the use of biological tissues of other nature and origin is not excluded. For example, it has been proposed to utilise as biological tissue a membrane of cranial or cervical dura mater taken from animals, or even a membrane of human or animal fascia lata.

After removal, the biological tissue is subjected to a cleaning operation. Subsequently there is effected a selection of the tissue with the intention that only the structurally most homogeneous and suitable parts of it are to be retained.

The selected layers of biological tissue are then subjected to a treatment operation intended to stabilise the elastic and mechanical strength thereof and to confer on them characteristics of chemical inertness with respect to blood.

These operations, generally known as "fixation" or "stabilisation" operations, are normally performed by immersing the tissue in solutions of glutaraldehydes with controlled pH, possibly enriched with anticalcifying additives.

The fixation operation generally involves the formation of stable cross links between the various forms of the glutaraldehyde and the aminic groups of the proteins constituting the collagen of the tissue.

The treatment times can vary widely in dependence on the characteristics of the biological tissue subjected to the fixation and the manner in which the fixation operation is performed. During the course of the treatment process, the concentration of the fixation solution is varied. For example, in the case in which solutions of glutaraldehyde are used, an initial phase, the said prefixation, is performed with a solution of glutaraldehyde in a concentration of the order of 0.2% which increases to a final fixation phase in which the concentrations are of the order of 0.5%.

For the purpose of understanding the invention it is necessary to distinguish between an incompletely fixed biological tissue (that is to say, a tissue subjected only to prefixation) and a completely fixed biological tissue. The incompletely fixed tissue in fact retains characteristics of plastic deformability which allow shaping operations to be performed thereon. The finally fixed tissue on the other hand has different elastic characteristics such that, after a possible deformation, the tissue tends to return spontaneously to the conformation assumed upon fixation.

Figure 4:
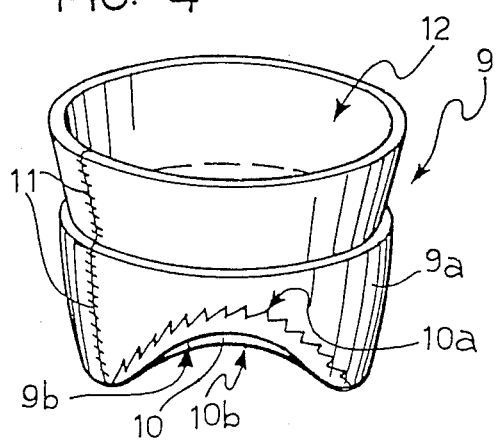
FIG. 4 is a perspective view of one of the elements of the prosthesis of FIGS. 1 to 3.
Figure 5:
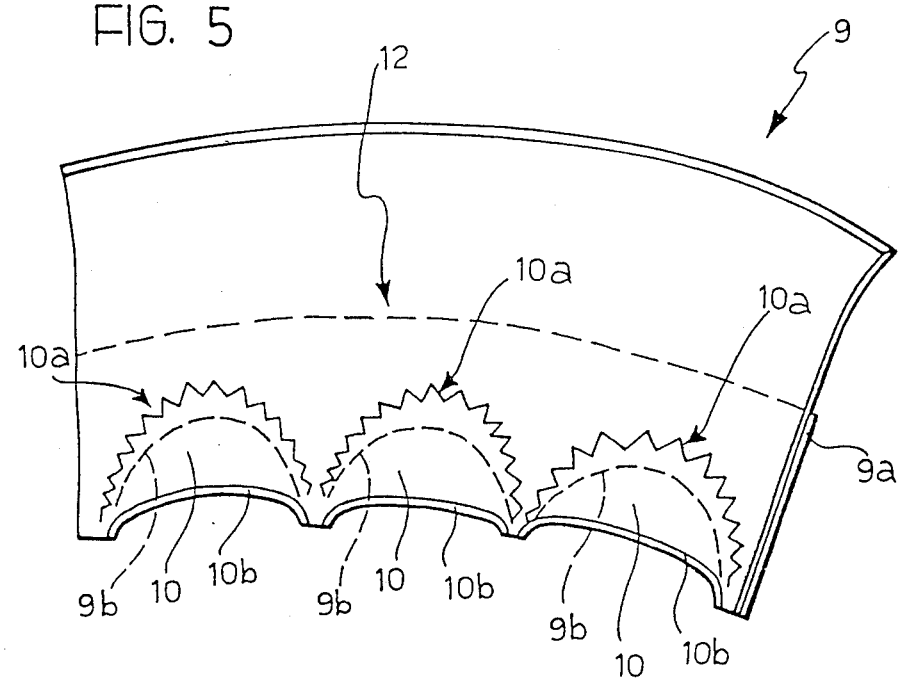
FIG. 5 illustrates an intermediate stage in the production of the element of FIG. 4.

As can be seen in FIGS. 4 and 5 which illustrate the sleeve 9 in the assembled configuration of the prosthesis and in open development, the sleeve 9 is constituted by two layers of biological tissue one of which (inner layer) constitutes the sleeve proper and is provided with shaped parts constituting valve flaps 10. The other layer of biological tissue (outer layer), indicated 9a, constitutes a tubular support covering for fixing the sleeve to the frame 2. For this purpose, in correspondence with the valve flaps 10 the layer 9a has crescent shape notches 9b the shape of which reproduce in development the shape of the sides of the projections 4 of the stent 3 of the prosthesis frame.

The two biological tissue layers constituting the sleeve 9 are sutured together with surgical thread along suture lines, preferably of the zig-zag type, which extend along crescent shape paths and each of which defines a crescent shape edge 10a of a respective valve flap 10. Preferably the thread utilised for the suture lines 10a is provided with a coating of biocompatible carbon material as described with reference to the textile 5.

In a manner which will be described in more detail below the valve flaps 10 have imparted to them a general bowl-shape configuration the concavity of which faces the layer 9a.

Consequently, when the two layers of biological tissue sutured together are wound into a tube by suturing together two opposite edges of the layers along a line of stitching indicated 11, the free edges of the valve flaps 10, indicated 10b, converge towards the interior of the sleeve, being arranged in a closely matching star shape configuration which can be seen in FIG. 2.

As can be seen in FIGS. 4 and 5 the sleeve has a generally frusto-conical configuration which, although not essential, has been found to be preferable for the functional purposes of the prosthesis.

The mounting of the sleeve 9 on the frame 2 is normally effected by suturing the layer 9a onto the cladding textile 5 along the end edges of the frame 3 and the projections 4 as is schematically illustrated in FIG. 3.

On the opposite side of the free edges 10b of the valve flaps 10 the inner layer of the sleeve is provided with a terminal portion 12 which extends beyond the corresponding end edge of the layer 9a and can be turned inwardly of the frame 2 and be sutured to the textile 5 adjacent the inner edge of the suture ring 6,7.

The conformation of the sleeve 9 and its disposition upon assembly within the frame 2 are such that substantially the whole of the surface of the prosthesis intended to be invested with the blood flow is covered with biological material having significant anti-thrombogenic properties.

Making reference, by way of example, to an atrioventricular implantation arrangement, in the diastolic phase the blood which flows out of the atrium enters the ventricle and traverses the prosthesis in the direction schematically indicated by the arrow in FIG. 1. In this direction of flow the blood flows over the convex face of the valve flaps 10, separating their free edges 10b and forming a substantially cylindrical central aperture in the prosthesis body, through which the blood can flow freely.

As soon as a pressure difference sufficient to cause the blood to flow in the opposite direction is established across the prosthesis by the effect of the contraction of the ventricle, the pressure exerted by the blood itself on the concave faces of the valve flaps 10 forces the free edges 10b into the closely matching position illustrated in FIG. 2. In these conditions the blood flow across the prosthesis is prevented.

In FIG. 6 there is generally indicated with the reference numeral 20 apparatus which can be used for shaping the valve flaps 10 of the biological tissue sleeve indicated by the reference numeral 9 in the preceding Figures.

The apparatus 20 includes a reservoir 21 intended to receive a solution L for the fixation of the biological tissue. The reservoir 21, (which is illustrated in median vertical section) has a generally drum-shape configuration and is constituted by a tubular peripheral wall 21a the openings at the ends of which are closed by a cover 21b and by a bottom wall 21c, constituted by plate elements of circular form. Between the cover 21b and the bottom wall 21c are interposed tie elements 21d which tightly hold the cover 21b and the bottom wall 21c onto the peripheral wall 21a ensuring fluid-prssure tight sealing of the reservoir 21.

The fixing solution L is taken from a collection reservoir 22 and conveyed into the reservoir 21 by means of a pump 23 through a duct 23a provided in the bottom wall of the reservoir 21. Between the pump 23 and the duct 23a there is interposed a valve 24 intended to prevent the return of the solution L towards the collection reservoir 22 when, as is described in greater detail below, the solution contained in the reservoir 21 is put under pressure.

The fixation solution L introduced into the reservoir 21 is in general a solution intended to perform the final fixation (terminal fixation) of a biological tissue, for example a 0.5% solution of glutaraldehyde.

In general, the rservoir 21 is not completely filled with the solution L. Above the free surface of the solution L there is thus defined a chamber 25 into which a gas under pressure derived from a source constituted, for example, by a gas bottle 26, can be admitted through an aperture 25a provided in the side wall of the reservoir 21.

In the connection pipe between the source 26 and the chamber 25 there is interposed a pressure regulator 27 which allows regulation of the gas pressure in the chamber 25, and, consequently, of the hydrostatic pressure of the solution L within the reservoir 21.

In the cover 21b of the reservoir 21 there are provided threaded apertures 28, each of which constitutes a seat for mounting a forming element 29, one of which is illustrated in greater detail in FIG. 7.

In the cover 21b there is normally provided a plurality of apertures 28, only one of which is visible in FIG. 6, which represents a section of the reservoir 21 taken on a diametral plane of the reservoir itself. The apertures 28 are distributed around a circular track concentric with the peripheral wall 21a of the reservoir. Each communicates through a respective radial duct 28a extending through the cover 21b with a collection cavity 128 formed in a central position in the wall of the cover 21b. The cavity 128 communicates with the suction side of a pump 129 the delivery side of which is connected to a breather duct which opens into the interior of the collection reservoir 22.

Each forming element 29 is substantially constituted by a frusto-conical body 30 having a tubular structure, supported at its larger base by a sleeve body 31 externally threaded at 31a. The inner cavity of the sleeve body 31 communicates with the inner cavity of the frusto-conical body 30. In the assembly disposition of the elements 29 in the reservoir 21 the sleeve body 31 of each element 29 is screwed into the associated aperture 28 in such a way that the tubular body 30 supported by it projects into the interior of the reservoir 21 so as to be substantially immersed in the fixing solution L when the reservoir 21 is filled.

At the end facing outwardly of the reservoir 21 each aperture 28 is closed by an insert 32 of transparent material (for example plexiglass) which allows the interior of the frusto-conical body 30 of the forming element 29 screwed into the aperture 28 to be observed from the outside.

The tubular body 30 of each forming element 29 has an intermediate body portion with three apertures 34 angularly adjacent one another and separated by shaped wall elements 35 extending axially with respect to the body 30 itself. Each element 35 has a generally flattened form in the radial direction with respect to the body 30, with a biconvex symmetrical shape. On the side facing outwardly of the body 30, each element 35 is delimited, for reasons which will be illustrated better below, by a rounded surface 35a free from sharp corners or other discontinuities.

At the end facing the sleeve body 31 each aperture 34 has a terminal edge 34a the shape of which reproduces the shape of the crescent-shape edges 10a of the valve flaps 10.

On the outer surface of the tubular body 30, above and below the apertures 34 respectively, there are provided annular grooves 36 the function of which will be illustrated below.

The apertures 34 and the grooves 36 are normally formed by mechanical working of the forming element 29, which is constituted by a single piece of plastics material such as the materials known by the commercial names "Teflon" or "Delrin".

The diametral dimensions of the frusto-conical body 30 of each forming element 29 are substantially identical with the diametral dimensions of the sleeves 9 which it is intended to make.

Figure 9:
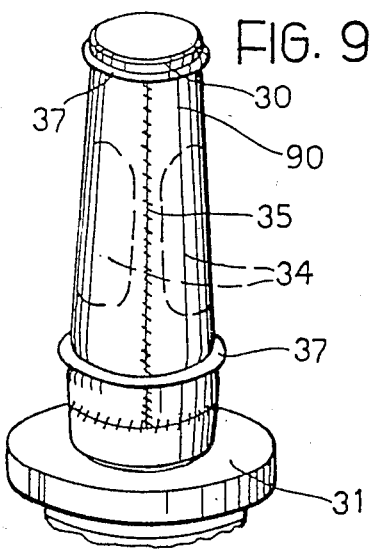

In use of the apparatus, sheets of incompletely fixed biological tissue, (that is to say sheets of biological tissue subjected only to the prefixation operation) are formed into a tube by suturing together two opposite edges of the sheet itself so as to form tubular sheets 90 of frusto-conical form which can be fitted over the bodies 30 of the elements 29 as is schematically illustrated in FIG. 9.

Figure 10:
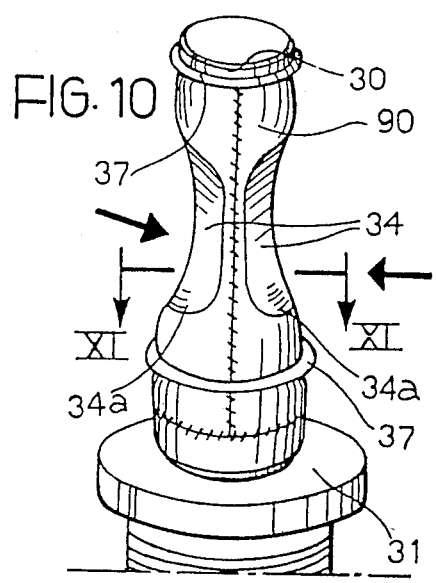

In both FIG. 9 and FIG. 10, only the portion of the forming element 29 comprising the body portion with the apertures 34 is illustrated. The dimensions of the sheath 90 are chosen in such a way that each sheath forms, with respect to the corresponding forming body 30, a loose coupling.

After having been fitted onto the forming body 30 each sheath 90 is securely fixed onto the forming element, for example by means of two resilient seals 37, of the type usually called "O rings" which engage the grooves 36. The suture line along which the sheath 90 has been closed into a tube is positioned in correspondence with one of the wall elements 35.

The sheath 90 is thus fitted with a fluid tight seal onto the associated body 30 in an arrangement in which the sheath portions extending across the apertures 34 constitute diaphragms which separate the internal cavities of the tubular body 30 from the exterior of the forming element 29.

Normally, the sheaths are mounted on the forming bodies 30 with the elements 29 fixed to the cover 21b of the reservoir 21 remote from the reservoir itself.

After having fitted the sheaths 90 onto the elements 29 and before finally locking the cover 21b onto the reservoir body 21, the pump 129 can now be activated for a short time in such a way as to create a vacuum within the cavities of the forming elements 29. Under the action of this vacuum the sheath portions 29 extending through the apertures 34 are, so to speak, "sucked" into the interior of the forming bodies. The deformed conformation thus assumed by such sheath portions can be seen through the transparent insert 32. It is thus immediately possible to detect the presence of defects (for example non-uniformity) and errors in mounting the sheaths 90 in such a way as to be able to replace defective sheaths and eliminate such mounting errors before proceeding to the shaping and fixation treatment of the biological tissue.

To effect such treatment the cover 21b carrying the elements 28 on which the sheaths 90 are sealingly fitted is closed over the reservoir 21 in the arrangement schematically illustrated in FIG. 6. The pump 23 is now activated making the fixation solution L flow into the interior of the reservoir 21. The level of the solution L is regulated in such a way that the whole of the sheath 90 is immersed in the fixation solution. Preferably a small quantity of solution L is also introduced into the interior of the forming bodies 30 in such a way as to act on the inner surface of the sheath 90.

After having closed and sealed the reservoir 21 the supply source 26 and the pressure regulator 27 are activated in such a way as to establish a controlled pressure within the solution L.

Figure 11:
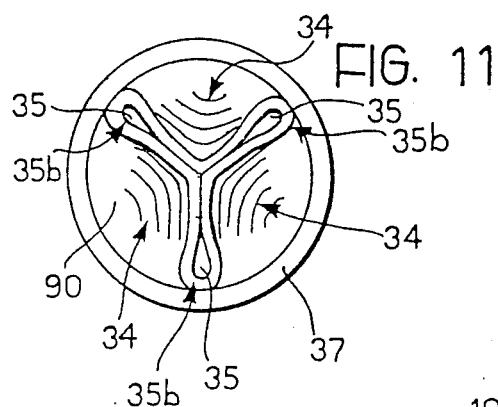

The pump 129 remains inoperative so that the inner cavity of each forming body 30 is practically at atmospheric pressure. Consequently the pressurisation of the solution L within the reservoir 21 is such that a pressure differential is established across the apertures 34, which causes deformation of the portions of the sheath 90 covering the apertures 34. The fixation solution acts on such sheath portions to dilate them and press them into the tubular body 30 in a disposition in which, as is schematically illustrated in FIG. 11, the median parts of such portions are positioned in mutual contact with a star-shape geometry substantially similar to that illustrated in FIG. 2 with reference to the valve flaps 10.

Naturally, the resistance afforded by the tissue of the sheath 90 to the pressure exerted by the fixation solution varies in dependence on the nature of the biological tissue, on its thickness and the dimensions of the apertures 34. The gas pressure within the interior of the chamber 25, which determines the pressure of the solution L, is regulated in such a way as to bring the deformed portions of the sheath to a configuration of mutual matched shaping substantially similar to that of the valve flaps 10 of the sleeve 9.

The instantaneous configuration reached by the deformed portion of the sheath 90 can be observed by an operator through the transparent inserts 32. It is therefore possible gradually to increase the pressure of the fixation solution until the configuration of mutual shape matching is positively achieved.

Each deformed portion of the sheath 90 then has a general bowl-shape configuration and is delimited on one side by a crescent-shape edge the shape of which reproduces the shape of the terminal edge 34a of the aperture 34 and, consequently, the crescent-shape edge 10a of one of the valve flaps 10. In other words, in each of the portions there is formed a shaped element of stably fixed biological tissue the conformation of which is exactly similar to the conformation of one of the valve flaps 10 of the sleeve 9.

The pressure difference which produces the deformation of the sheath 90 is maintained for the period necessary to produce complete fixation of the biological tissue of the sheath 90 by the solution L.

According to the invention the biological tissue intended to constitute the sleeve 9, and in particular the valve flap 10, is subjected to a shaping operation which makes it assume the final conformation of use when the tissue is still not completely fixed. The final or complete fixation is effected when the biological tissue has already been deformed making it assume the final conformation of use.

In this way the fixed biological tissue tends to reassume, after any accidental deformation, the conformation in which the tissue was mounted in the prosthesis in the form of a valve flap.

Moreover, the existence of a pressure gradient across the deformed portions of the sheath 90 encourages the diffusion of the fixation solution L across the biological tissue ensuring an intimate penetration thereof into the tissue. This also allows the treatment times necessary to obtain final fixation of the tissue to be significantly reduced.

The effect of the pressure gradient which is established across these deformed portions is that the solution L in fact seeps through the biological tissue, penetrating into the tubular body 30 of the forming element 29.

The duration of the fixation operation can be chosen in dependence on the pressure at which the solution L is delivered (that is to say, in dependence on the pressure gradient applied across the two faces of each portion of the sheath 90 extending across one of the apertures 34) in such a way that the deformed portions of the sheath 90 are intimately permeated by the solution L.

Further, the fact that the portions of the sheath 90 intended to constitute the valve flaps 10 of the sleeve 9 assume their final conformation under the action of a fluid under pressure permits the shaping of such flaps whilst the flaps themselves are subjected to a pressure range which substantially reproduces the pressure range to which the flaps are subjected in use. In this way, upon final fixation of the biological tissue, there is obtained a mutual shape-matching configuration between the flaps which can be exactly reproduced in the conditions of use. This also avoids the possibility of non-uniform stresses and strains arising in such portions which could prejudice the correct operation of the prosthetic valve flaps. The conformation of the wall elements 35 and, in particular, the presence of the rounded surfaces 35a on the radially outer side of each element avoids the possibility of stress phenomena or lesions arising during the shaping and final fixation operation in the regions of biological tissue stretched out over the elements 35, such as would prejudice the strength of the tissue.

In the preceding part of the description, explanation has been given with reference to a situation of use of the apparatus 20 in which the pressure gradient applied between the opposite faces of each of the portions of biological tissue defining the valve flaps 10 is exclusively derived from the pressure applied to the fixation solution L within the reservoir 21. It is, however also possible to establish the said pressure gradient by the effect of a combined action of the pressure applied to the fixation solution L and the vacuum created within the cavity of each shaping element 29 by the pump 129. In this case the pump 129, which allows (as previously described) a preliminary control of the structural characteristics and the exact positioning of the sheaths 90 mounted on the shaping elements 29, is also activated during the final fixation operation on the biological tissue, by jointly adjusting the effect of pressurisation of the solution L by the gas taken from the source 26 and the degree of vacuum generated within the shaping elements 29 by the pump 129.

It is also possible to envisage the use of apparatus 20 in which the pressurisation system formed by the gas source 26 and the regulator 27 is eliminated. In this case the pump 129 is activated both to perform a preliminary check on the structural characteristics and exact positioning of the sheaths 90 mounted on the shaping elements 29, and to generate, after the reservoir 21 has been filled with the fixation solution L, the pressure gradient which determines the deformation of the portions of biological tissue extending across the apertures 34.

In structural terms, the said gradient can be established in at least three different ways, that is to say:

(i) by applying (for example by means of gas taken from the source 26) a pressure to the fixation solution L within the reservoir 21, maintaining the internal cavities of the forming elements 29 substantially at atmospheric pressure, (ii) by applying the said pressure to the fixation solution L and simultaneously creating (for example by operation of the pump 129) a vacuum (a pressure less than atmospheric pressure) in the interior cavity of the forming elements 29, and (iii) exclusively by the effect of the vacuum created in the interior cavities of the forming elements 29, whilst the solution L is maintained at substantially atmospheric pressure.

Upon completion of the fixation operation, the sources which caused the said pressure gradient are de-activated and the cover 21a is removed from the reservoir 21. The sheaths 90 can then be disengaged from the forming elements 29 by removing the sealing rings 27.

Figure 12:
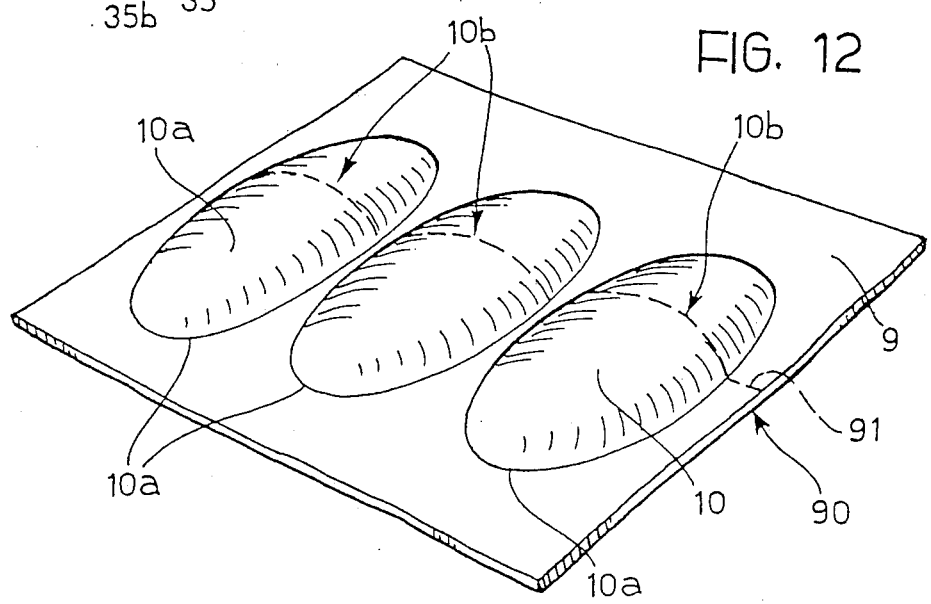

After the removal of the stitches previously applied to effect the closure into tubular form, the sheet constituting each sheath 90 is again opened out, assuming the conformation schematically illustrated in FIG. 12, in which the sheet of biological material, initially flat, now has three bowl-shaped parts substantially equal to one another and delimited on corresponding sides by crescent shape edges constituting the crescent edges 10a.

In other words, the sheet of biological tissue obtained starting from the sheath 90 subjected to the final fixation treatment incorporates a valve sleeve provided with three completely formed and shaped flaps 10.

The separation of the biological tissue of the sheath 90 along a line 91 which joins the ends of the crescent shaped edges 10a permits the separation of the frustoconical sleeve from the remaining part of the sheath 90 intended to be discarded, forming the free edges 10b of the valve flaps 10.

In the illustrated embodiment the separation of the biological tissue of the sheath 90 is effected after the sheath 90 has been released from the forming element 29 and returned to an open position. It is, however, possible to effect separation of the sheath 90 when it is still closed in the form of a tube, possibly when it is still fitted onto the forming element 29.

The valve sleeve 9 is subsequently mounted on the prosthesis according to the criteria described in the introductory portion of the present description.

What is claimed is:

1. Apparatus for the manufacture of valve flaps for a cardiac prosthesis of the kind comprising a frame which can be traversed by blood flow and a sleeve of biological tissue with a plurality of valve flaps anchored to the frame along respective crescent shaped edges and provided with free edges projecting into the frame and which can be separated by blood flowing through the prosthesis in one direction and which can prevent the flow of blood in the opposite direction by moving to closely matching positions under the pressure exerted by the blood itself, wherein the apparatus comprises:

a reservoir which can be filled with a fluid for the fixation of biological tissue;

at least one forming element projecting into said reservoir in a position for immersion in said fixation fluid, said forming element being substantially tubular and having a peripheral wall defining plural elongated through apertures, edges of said wall defining said apertures being sloped from the outside toward the inside of said element and free from sharp edges, and means for forming a reduced pressure within said at least one forming element as compared with pressure outside of said element, surfaces defining said apertures being of a configuration suitable for forming said crescent shaped edges of a heart valve.

2. Apparatus as defined in claim 1, wherein the shaped wall elements are of generally flattened form, oriented in a radial direction with respect to the forming element and are delimited, on the radially outer side, by a substantially discontinuity-free surface.

3. Apparatus as defined in claim 1, wherein the said forming element has, at least in the region in which the said apertures are provided, a frustoconical shape.

4. Apparatus as defined in claim 1, wherein the reservoir has associated therewith a source of gas under pressure selectively adjustable to introduce gas under controlled pressure into the reservoir above the free surface of the fixation liquid in the said reservoir in use of the apparatus.

5. Apparatus as defined in claim 1, including a vacuum generator and means connecting the vacuum generator to the interior cavity of each said forming element.

6. Apparatus as defined in claim 1, wherein the said reservoir includes a cover having holes each of which forms a mounting seat for an associated forming element each of the said holes being associated with a transparent fluid-tight closure member which allows observation of the interior cavity of the associated forming element.

7. Apparatus as defined in claim 6, including a vacuum generator and wherein the said cover is provided with ducts communicating with said holes for putting said vacuum generator into communication with the interior cavity of each said forming element.

8. Apparatus as defined in claim 1, wherein said apertures are so spaced peripherally about said forming element that a sheath of biological tissue covering the apertures and deformed to protrude inward through the apertures by a reduction of pressure within said forming element brings the deformed portions of the sheath of biological tissue into a configuration of mutual matched shaping substantially similar to flaps of a heart valve.

* * * * *